US006436430B1

(12) United States Patent
Mulye

(10) Patent No.: US 6,436,430 B1
(45) Date of Patent: Aug. 20, 2002

(54) SELF-EMULSIFYING COMPOSITIONS FOR DRUGS POORLY SOLUBLE IN WATER

(75) Inventor: Nirmal Mulye, Long Beach, NY (US)

(73) Assignee: Pharmasolutions, Inc., Cranbury, NJ (US)

( * ) Notice: Subject to any disclaimer, the term of this patent is extended or adjusted under 35 U.S.C. 154(b) by 0 days.

(21) Appl. No.: 09/459,299

(22) Filed: Dec. 10, 1999

Related U.S. Application Data

(60) Provisional application No. 60/111,951, filed on Dec. 11, 1998.

(51) Int. Cl.[7] .......................... A61K 47/00; A61K 9/20; A61K 31/21; A01N 37/00
(52) U.S. Cl. ....................... 424/439; 424/464; 514/506; 514/937
(58) Field of Search ................................. 424/439, 464; 514/506, 937

(56) References Cited

U.S. PATENT DOCUMENTS

| | | | |
|---|---|---|---|
| 4,388,307 A | 6/1983 | Cavanak | |
| 4,874,795 A | 10/1989 | Yesair | |
| 4,970,076 A | 11/1990 | Horrobin | |
| 4,990,337 A | 2/1991 | Kurihara et al. | |
| 4,996,193 A | 2/1991 | Hewitt et al. | |
| 5,139,997 A | 8/1992 | Bach et al. | |
| 5,154,930 A | 10/1992 | Popescu et al. | |
| 5,206,219 A | 4/1993 | Desai | |
| 5,342,625 A | 8/1994 | Hauer et al. | |
| 5,391,377 A | 2/1995 | Barnwell | |
| 5,430,021 A | 7/1995 | Rudnic et al. | |
| 5,484,801 A | 1/1996 | Al-Razzak et al. | |
| 5,583,153 A | * 12/1996 | Brahn ........................ | 514/449 |
| 5,597,562 A | * 1/1997 | Nomura et al. ............ | 424/85.1 |
| 5,639,724 A | 6/1997 | Cavanak | |
| 5,645,856 A | 7/1997 | Lacy et al. | |
| 5,650,172 A | 7/1997 | Matsuda et al. | |
| 5,759,997 A | 6/1998 | Cavanak | |
| 5,807,820 A | 9/1998 | Elias | |
| 5,824,638 A | 10/1998 | Burnside et al. | |
| 5,858,401 A | 1/1999 | Bhalani et al. | |
| 5,897,876 A | 4/1999 | Rudic et al. | |
| 5,919,459 A | 7/1999 | Nacy et al. | |
| 5,962,014 A | * 10/1999 | Hauer et al. ................ | 424/450 |
| 5,962,017 A | 10/1999 | Hauer et al. | |
| 6,057,289 A | * 5/2000 | Mulye ......................... | 514/11 |
| 6,096,338 A | * 8/2000 | Lacy et al. .................. | 424/455 |
| 6,106,848 A | * 8/2000 | Preuilh et al. .............. | 424/401 |

FOREIGN PATENT DOCUMENTS

| | | |
|---|---|---|
| EP | 0 813 876 A1 | 12/1997 |
| WO | WO 98/40051 | 9/1998 |
| WO | WO 98/40094 | 9/1998 |

* cited by examiner

Primary Examiner—Russell Travers
Assistant Examiner—Lauren Q. Wells
(74) Attorney, Agent, or Firm—Scully, Scott, Murphy & Presser

(57) ABSTRACT

The present invention is directed to a pharmaceutical composition comprising a pharmaceutically effective amount of a lipophilic drug, in association with a pharmaceutical carrier, said carrier comprising a lipophilic drug solubilizing effective amount of a propylene glycol monoester of $C_6$–$C_{18}$ fatty acid having at least 60% by weight monoester based on the total weight of the propylene glycol ester and a non-ionic surfactant.

26 Claims, No Drawings

SELF-EMULSIFYING COMPOSITIONS FOR DRUGS POORLY SOLUBLE IN WATER

RELATED APPLICATIONS

The present application is claiming benefit of the provisional application, U.S. Ser. No. 60/111,951 filed on Dec. 11, 1998.

FIELD OF INVENTION

The present invention relates to a pharmaceutical composition comprising a lipophilic drug, which is substantially non-soluble in water.

BACKGROUND OF THE INVENTION

Many of the drugs in pharmaceutical compositions are lipophilic, i.e., substantially insoluble in aqueous solution. As a result, there are several problems associated with administration thereof to a patient, such as a mammal. These problems are best illustrated with a representative lipophilic drug, the cyclosporins.

The Cyclosporins comprise a class of structurally distinctive, cyclic, poly-N-Methylated undecapeptides, commonly possessing pharmacological, in particular immunosuppressive, anti-inflammatory and/or anti-parasitic (in particular anti-protozoal, e.g. anti-malarial) activity. The first of the Cyclosporins to be isolated was the naturally occurring fungal metabolite Ciclosporin or Cyclosporine, also known as cyclosporin A and commercially available under the Registered Trademark SANDIMMUN® or SANDIMMUNE®.

Cyclosporin is highly lipophillic and hydrophobic. Therefore, cyclosporin is sparingly soluble in water, but dissolves readily in organic solvents, such as methanol, chloroform and the like. Due to its limited solubility in water, the bioavailability of orally administered cyclosporin is extremely low and may be highly dependent on the condition of the patient. Accordingly, it is very difficult to retain an effective therapeutic concentration. Cyclosporin can thus be formulated into a preparation for oral administration only with great difficulty. Accordingly, numerous studies have been extensively conducted to find a cyclosporin preparation effective for oral administration, that is, a preparation which provides both uniform dosage and bioavailability of the active component.

In the prior art preparations of cyclosporin suitable for oral administration, sparingly water-soluble cyclosporin has been usually formulated in the form of an emulsion by combining cyclosporin with a surfactant, an oil and a co-surfactant. For example, U.S. Pat. No. 4,388,307 discloses a liquid formulation of cyclosporin that includes at least one of the following components: (a) a transesterification product of a natural or hydrogenated vegetable oil and a polyalkylene polyol; (b) a saturated fatty acid triglyceride; or (c) a monoor diglyceride. Component (a) is formed by the transesterification of a triglyceride, e.g., a triglycerides from a vegetable oil, with polyethylene glycol. Component (b) may be obtained by esterifying a triglyceride with saturated fatty acid while component (c) is a mono- or di-glyceride, or a mono- or di-fatty acid glyceride. In these prior art formulations, it is preferred that ethanol be further used as a solubilizing agent. However, since this liquid formulation is administered as an aqueous solution, it is both inconvenient and difficult to administer in an uniform dosage as a result of its limited solubility in water.

In order to mitigate the inconvenience of diluting a cyclosporin liquid composition with water prior to oral administration, a liquid composition has been formulated into a soft capsule preparation, which is now commercially available as SANDIMMUN®. In this preparation, the cyclosporin soft capsule contains a large amount of ethanol as a cosurfactant in order to solubilize the cyclosporin. However, since ethanol permeates the gelatin shell of the capsule and is volatile even at normal temperatures, the constitutional ratio of the contents of the soft capsules may greatly vary during storage. The resulting reduced ethanol content may in turn result in crystallization of the cyclosporin and thus results in a significant variation in the bioavailability of cyclosporin. The variation in cyclosporin concentration in this formulation makes it quite difficult to determine the dosage needed to provide a desired therapeutic effect.

Belgian Patent No. 895,724, which relates to the use of Cyclosporin in the treatment of multiple sclerosis, also describes two oral formulations suitable for the administration of this particular compound. Both of these are based on the commercial Cyclosporin (SANDIMMUN®) drink-solution, with adaption to suit the particular cyclosporin active ingredient. The first comprises 5–10% Cyclosporin, 10–12% ethanol, 30–40% MAISINE®, about 4% CREMOPHORE® and 51–30% LABRAFIL®. This corresponds to the composition of the liquid oral formulation of SANDIMMUN®, but with the replacement of the natural vegetable oil component with MAISINE® and the introduction of a minor percentage of the tenside CREMOPHORE®. MAISINE® is a trans-esterification product of corn oil with glycerol. The ratio of Cyclosporin: tenside in the disclosed composition is 1:0.4–0.8. Inasmuch as ethanol is a key component of the formulation, it does not make any suggestion to replace ethanol as co-solvent/cosurfactant.

U.S. Pat. No. 5,342,625 discloses cyclosporin in association with a hydrophilic phase, lipophilic phase and a surfactant. The hydrophilic phase comprises 1,2-propylene glycol or $R_1$—[O—$(CH_2)_x$]—$OR_2$, where $R_1$ is alkyl containing 1–5 carbon atoms or tetrahydrofuryl, $R_2$ is hydrogen, alkyl containing 1–5 carbon atoms or tetrahydrofurfuryl and x is 1–6. Such ethers are commercially available under the trade name of Transcutol and Glycofurol; in addition, it may contain $C_{1-5}$ alkanols, such as ethanols.

However, the use of ethanol as well as other hydrophilic solvents such as 1,2-propylene glycol or liquid polyethylene glycols in these sorts of systems creates several problems. Since ethanol permeates the gelatin shell of the capsule and is volatile, even at room temperature, the constitutional ratio of the contents of the soft capsules may greatly vary during storage. The resulting reduced ethanol content may in turn result in crystallization of the cyclosporin, and this results in a significant variation in the bioavailability of cyclosporin when administered to an animal. The variation in cyclosporin concentrate in these types of formulations makes it quite difficult to determine the dosage needed to provide a desired therapeutic effect. Moreover, when solvents such as ethanol, 1,2-propylene glycol and liquid polyethylene glycols are utilized in gelatin capsules, these solvents have a tendency to absorb moisture, thereby rendering brittle the shell walls, especially those in hard gelatin capsules, and thereby resulting in leakage of the contents of the capsules during storage or shipment. Moreover, one of the biggest drawbacks using hydrophilic components, as in U.S. Pat. No. 5,342,625, has been the potential of reprecipitation of the drug from the formulation when it comes into contact with aqueous systems, such as in the stomach or intestine after ingestion by the mammal.

Moreover, the complexity of the ternary formulations as in U.S. Pat. No. 5,342,625 makes them costly and difficult to manufacture. Moreover, U.S. Pat. No. 5,342,625 suggests the use of solvents such as Glycofurol and Transcutol which are restricted for pharmaceutical use by several regulatory agencies worldwide, including the FDA, because they are not considered "Generally Recognized As Safe" (GRAS) for oral use. Further, with hydrophilic solvents there is always an added risk of precipitation of the cyclosporin on exposure to gastrointestinal fluids in vivo, thereby further affecting bioavailability.

U.S. Pat. No. 4,970,076 discloses the use of GLA (gamma linoleic acid) and DGLA (dihomogammalinolenic acid) and their derivatives as active components in pharmaceutical compositions to counter the adverse side effects of cyclosporin, such as nephrotoxicity and renal side effects. It, however, does not teach or even recognize the use of the lipophilic materials for enhancing the solubility, bioavailability, emulsion or microemulsion capability.

A couple of very recent patents, U.S. Pat. Nos. 5,759,997 and 5,858,401, disclose the use of a mixture of mono-,di-and triglycerides as a carrier for cyclosporin formulations. The formulations therein do not contain a hydrophilic component, such as alcohol, propylene glycol, and the like. However, the formulation therein has several drawbacks. For example, some of the problems encountered with these formulations include the limited solubility of cyclosporin therein. As a result, the size of the capsules necessary to accommodate the required dose, e.g., 100 mg, is very large. This causes a major inconvenience to the patient, resulting in a larger pill or capsule, thereby making it more difficult for the patient to swallow the same. This, in turn, tends to minimize compliance by the patients who have to take multiple capsules per day.

Furthermore, in addition, the stability of this formulation, especially those having a high monoglyceride content when used in hard gelatin capsules, is extremely limited; monoglycerides have a tendency to make the gelatin shells brittle, causing leakage of the contents of such capsules.

It is apparent that there is a need to prepare formulations of lipophilic drugs, which minimize the number of components that are to be administered to the patient. There is also a need to prepare formulations of lipophilic drugs which provide higher drug loading, and therefore need smaller size capsules, use components considered as GRAS and offer advantageous formulation stabilities, desirable pharmokinetics and bioavailability and ease of manufacture.

In accordance with the present invention, it is now surprisingly been found that pharmaceutical compositions comprising lipophilic drugs can be prepared which can overcome the difficulty in dosing and patient compliance/acceptability encountered in the art as discussed above. More specifically, it has been found that the use of a specific lipophilic carrier system comprising esters of propylene glycol with $C_6$–$C_{18}$ fatty acids containing at least about 60% by weight monoesters based on the total weight of the propylene glycol ester in conjunction with a non-ionic surfactant overcomes the problems described hereinabove. No one heretofore utilized or realized the advantages of this specific lipophilic carrier system in combination with lipophilic drugs. Unlike the composition of the prior art containing mono-, di- or triglycerides of vegetable oils, the propylene glycol esters of fatty acids containing levels of monoester indicated hereinabove are more compatible with oral dosage forms, such as those involving gelatin capsules.

It has been found that by employing the above defined carrier system, it is possible to obtain lipid-based formulations which do not require any additional solvent or co-solvent, such as alcohol, propylene glycol, polyethylene glycol, etc., and therefore, problems associated with these hydrophilic components or solvents mentioned hereinabove are eliminated. Thus, the compositions of the present invention are more stable than those compositions associated with hydrophilic components, such as alcohols.

Due to the greater solubility of lipophilic drugs in the carrier of the present invention, the size of the capsule for the delivery of unit doses of the lipophilic drug is reduced, providing greater patient acceptance and compliance. Moreover, if the oral dosage form is a capsule, there is an excellent compatibility of the propylene glycol ester having at least 60% by weight monoesters of $C_6$–$C_{18}$ fatty acids based on the total weight of the ester with a hard or soft shell gelatin capsule or with a non-gelatin capsule, thereby preventing brittleness and leakage of the formulation during storage. Furthermore, the present composition forms a microemulsion upon exposure to aqueous fluid (water, in e.g., the g.i. tract) which will provide higher and uniform bioavailability. This characteristic will further help reduce the intra- and inter-subject variability associated with the absorption of lipophilic drugs, as well as minimize the effect of food on the absorption and bioavailability of these drugs in mammals.

SUMMARY OF THE INVENTION

The present invention is directed to a pharmaceutical composition comprising a pharmaceutically effective amount of a lipophilic drug in association with a carrier, said carrier comprising a mixture of a propylene glycol ester of $C_6$–$C_{18}$ fatty acids having at least about 60% by weight monoesters based on the total weight of the propylene glycol ester in an amount sufficient to solubilize the lipophilic drug, and a non-ionic surfactant, said surfactant being present in an amount sufficient to form a microemulsion with the lipophilic drug and propylene glycol monoester when in contact with an aqueous medium, especially those found in mammals.

The present invention is also directed to the pharmaceutically acceptable carrier described hereinabove. Furthermore, the present invention is also directed to a method of forming a microemulsion of a pharmaceutical composition containing a lipophilic drug as the active ingredient, said method comprising (a) thoroughly mixing said lipophilic drug with (i) a drug solubilizing effective amount of a propylene glycol ester of $C_6$–$C_{18}$ fatty acid with at least 60% by weight of monoester based on the total weight of the propylene glycol ester; and (ii) a non-ionic surfactant having a HLB value greater than 10, said surfactant being present in sufficient amounts to form a microemulsion with said lipophilic drug and said propylene glycol ester when brought in contact with an aqueous medium, as for example, in a mammal and (b) contacting the pharmaceutical composition prepared in (a) with an aqueous medium.

The present invention is also directed to a method of orally administering a pharmaceutical composition containing a lipophilic drug to a patient in need thereof, comprising orally administering to said patient a pharmaceutical composition comprising a pharmaceutically effective amount of a lipophilic drug, a drug solubilizing effective amount of a propylene glycol ester of $C_6$–$C_{18}$ fatty acid having at least 60% by weight monoester based on the total weight of the propylene glycol ester and a sufficient amount of a non-ionic surfactant having HLB greater than 10, said surfactant being present in sufficient amount to form a microemulsion with said lipophilic drug and said propylene glycol ester when brought in contact with an aqueous medium, such as water.

The present invention is also directed to a method of increasing the drug loading ability of a lipophilic drug in a pharmaceutical composition comprising thoroughly mixing a pharmaceutically effective amount of a said lipophilic drug with a drug solubilizing effective amount of a propylene glycol ester of $C_6$–$C_{18}$ fatty acid with at least 60% by weight monoester based on the total weight of the propylene glycol ester and a sufficient amount of a non-ionic surfactant having a HLB greater than 10, said surfactant being present in sufficient amount to form a microemulsion with said lipophilic drug and said propylene glycol ester when brought into contact with water.

Another aspect of the present invention is directed to a method of enhancing the bioavailability of a lipophilic drug in a patient in need of drug therapy, said method comprising orally administering to said patient a pharmaceutical composition comprising a therapeutically effective amount of said drug in association with a carrier said carrier comprising (a) a drug solubilizing effective amount of a propylene glycol ester of $C_6$–$C_{18}$ fatty acid with at least 60% by weight monoester based on the total weight of the propylene glycol ester and (b) a non-ionic surfactant having a HLB value greater than 10, said surfactant being present in sufficient quantity to form a microemulsion with said drug and propylene glycol ester when brought in contact with an aqueous medium. Moreover, the present invention is directed to a method of forming a pharmaceutical composition containing a lipophilic drug as the active therapeutic agent, which comprises thoroughly mixing the lipophilic drug with the carrier, as defined herein, which when brought in contact with an aqueous medium forms a microemulsion.

DETAILED DESCRIPTION OF THE INVENTION

The term "carrier" is a term of art. As used herein, the term "carrier" refers to the composition that transports the medicament across the biological membrane or within a biological fluid. The carrier of the present invention comprises (a) the propylene glycol ester of $C_6$–$C_{18}$ fatty acid, having at least 60% by weight monoester, based on the total weight of the propylene glycol ester, (b) the surfactant and (c) optionally other adjuvants that normally are present therein, as described hereinbelow.

As indicated hereinabove, an aspect of the present invention relates to a pharmaceutically acceptable carrier in association with a lipophilic drug in a pharmaceutical formulation. It is preferred that the formulation be used in oral dosage form, e.g., in hard or soft gelatin capsules (or capsules made of other materials such as starch, cellulose or its derivatives, and the like).

The term "lipophilic" as used herein is a term of art. Lipophilic molecules, as defined herein, are those having a partition coefficient (log p) in octanol/water or n-octanol/saline of greater than 1. The drugs contemplated to be used in the present invention and in association with the carrier of the present invention are lipophilic medicaments, i.e., drugs which are substantially insoluble in water at 25° C. The preferred drugs have a log p ranging from about 1 to about 5 and more preferably ranging from about 1.25 to about 3.5.

The carrier described herein is associated with the lipophilic drug or therapeutic agent. As used herein, the terms "drug", "therapeutic", "therapeutic agent", "medicament" and "active ingredient" are synonymous and are used interchangeably. It can be any type of medication which is lipophilic, as defined herein, which acts locally in the mouth or acts systemically, which in the case of the latter, can be administered orally, to transmit the active component into the gastrointestinal tract and into the blood, fluids, and tissues of the body. Representative active medicaments used in the present invention include lipophilic drugs which are antacids, anti-inflammatory substances, coronary vasodilators, cerebral vasodilators, psychotropics, antineoplastics, stimulants, anti-histamines, laxatives, decongestants, vitamins, gastrointestinals, anti-diarrheal preparations, antianginal drugs, vasodilators, anti-arrythmics, anti-hypertensive drugs, vasoconstrictors, anti-migraine drugs, anti-coagulants and anti-thrombotic drugs, analgesics, anti-pyretics, hypnotics, sedatives, anti-emetics, anti-nauseants, anticonvulsants, anti-epileptics, neuromuscular drugs, drugs acting on CNS (Central Nervous System), hyper- and hypoglycemic agents, thyroid and anti-thyroid preparations, diuretics, anti-spasmodics, uterine relaxants, mineral and nutritional additives, anti-obesity drugs, anabolic drugs, anti-asthmatics, expectorants, cough suppressants, mucolytics, anti-uricemic drugs, and other drugs or substances acting locally in the mouth, such as topical analgesics, local anaesthetics, or combination thereof and the like. The present formulation may contain a combination of more than one active ingredient.

The preferred active ingredients are macrolides, such as rapamycins, clavulanic acid, including its potassium salt and erythromycin and derivatives thereof, such as erythromycin acistrate, erythromycin estolate, erythromycin glucoheptonate, erythromycin lactobionate, erythromycin propionate, erythromycin stearate, and the like; immunosuppressive agents, like cyclosporin and rapamycins; non-steroidal anti-inflammatory agents, such as Ibuprofen and Naproxen; Paclitaxel; Hydrochlorothiazide; anti-fungal agents, such as Itraconazole; osteoporosis drugs, such as alendronate sodium.

In a preferred embodiment of the present invention, the pharmaceutical formulation is substantially free and more preferably completely free of ethanol and other hydrophilic components. It is also preferred that the pharmaceutical composition is substantially free and more preferably completely free of fatty acid triglycerides.

In a preferred embodiment, the present invention relates to a pharmaceutical formulation in the absence of a hydrophilic component, such as ethanol in oral dosage form, and in the absence of fatty acid triglycerides e.g., in hard or soft gelatin capsules (or capsules made of other materials such as starch, cellulose or its derivatives, etc.) or in a parental preparation for intra-muscular and intravenous administration.

The active ingredient is present in the present formulation in pharmaceutically effective amounts. Of course those of ordinary skill in the art will understand that the amounts of active ingredient present in the composition will vary with the particular situation, including without limitation, the mode of administration, the size, age and condition of the subject and the like. Moreover, these effective amounts will be easily determined by the physician without an undue amount of experimentation. It is preferred that the active ingredient is present in amounts ranging from 0.01% to 50% by weight of the composition and more preferably in an amount ranging between 5% and 40% by weight.

The second essential component of the present composition is the lipid, i.e., the propylene glycol esters of $C_6$–$C_{18}$ fatty acids with greater than or equal to about 60% by weight monoesters based on the total weight of the propylene glycol ester utilized. When using the term "propylene glycol ester" herein, it is to be understood that it refers to this lipid, as defined hereinabove.

The term propylene glycol refers to 1,2-dihydroxypropane as well as 1,3-dihydroxypropane. The preferred propylene glycol is 1,2-dihydroxypropane.

The fatty acids of the propylene glycol ester utilized in the present invention contain $C_6$–$C_{18}$ carbon atoms. They may contain carbon-carbon double bonds. If a carbon-carbon double bond is present, it is preferred that it does not contain more than nine carbon-carbon double bond and more preferably no more than four carbon-carbon double bonds. If a carbon-carbon double bond is present, it is more preferred that the fatty acid contains 1, 2 or 3 carbon-carbon double bonds. The fatty acids utilized herein preferably have the formula RCOOH, wherein R is a hydrocarbyl group (group containing carbon and hydrogen atoms) containing 6–18 carbon atoms, which hydrocarbyl group is saturated. Although the fatty acid may be branched, it is preferred that a straight chain fatty acid is utilized.

Moreover, it is preferred that the fatty acid of the propylene glycol monoester contains 6–16 carbon atoms, and more preferably 8–12 carbon atoms, and most preferably 8–10 carbon atoms, and even more preferably 8 or 10 carbon atoms. It is also preferred that the fatty acid contains an even number of carbon atoms. It may contain at least one carbon-carbon double bond, but it is preferred that, in these preferred embodiments, the fatty acid contains no carbon-carbon double bonds. It is also preferred that in these preferred embodiments, the fatty acid of propylene glycol ester is a straight chain.

The second component, as indicated hereinabove, is a lipid fatty acid esterified product of propylene glycol containing at least about 60% monoester based on the total weight of propylene glycol ester, i.e., only one of the hydroxy groups is esterified. The term "ester of propylene glycol containing at least about 60% monoester by weight" signifies that at least about 60% by weight up to a maximum of 100% of the esters formed in the esterification reaction is the monoester. Although the second component may contain any amount of monoester above the about 60% level based on the total weight of the propylene glycol ester, including 60%–100% inclusive, e.g. including at least 60%, 65%, 70%, 75%, 80%, 85%, 90%, 95%, 98% or 99% by weight, it is preferred that the propylene glycol ester contains at least about 70% by weight monoester, and most preferably at least about 90% by weight monoester. However, in a preferred embodiment, it contains at least about 95% by weight monoester and in another preferred embodiment, at least about 99% by weight monoester.

Although a mixture of fatty acids of $C_6$–$C_{18}$ may be used to be esterified to the propylene glycol, it is preferred that only one type of fatty acid be esterified to the propylene glycol.

The esters of propylene glycols used in the present invention are commercially available or are prepared by art-recognized techniques, e.g., by esterification of propylene glycol with fatty acids. Examples of propylene glycol esters useful in the present invention which are commercially available is propylene glycol monocaprylate, and the like. As indicated hereinabove, it is preferred that the propylene glycol monocaprylate and other propylene glycol esters used herein contain the monoester in amounts ranging from about 60% to 100% inclusive.

The propylene glycol esters of $C_6$–$C_{18}$ fatty acid with at least about 60% by weight of monoester based on the total weight of propylene glycol ester of the fatty acids are used as the lipids in the carrier.

They help to solubilize the lipophilic drug. The propylene glycol esters used in the present invention having at least 60% monoester content by weight will also be designated as the "lipophilic drug solubilizing agent", or "solubilizing agent" or "lipid", and these terms will also be used to denote the propylene glycol monoester having at least 60% monoester.

Thus, in the composition of the present invention, it is preferred that the propylene glycol ester of $C_6$–$C_{18}$ fatty acid with at least about 60% by weight of monoester based on the total weight of propylene glycol ester be present in amounts sufficient to solubilize the lipophilic drug. Preferably, the weight ratio of lipophilic drug to propylene glycol ester described hereinabove ranges from about 1:0.5 to about 1:500, and more preferably ranges from about 1:1 to about 1:20 and even more preferably from about 1:1 to about 1:4 and most preferably, the lipophilic drug and propylene glycol ester are present in a weight ratio of about 1:2 or 1:3.

As indicated hereinabove, the lipids utilized in the present invention are present in amounts sufficient to solubilize the lipophilic drugs in the pharmaceutical composition.

To maximally solubilize lipophilic drugs, it is preferred that the lipophilicity of the lipophilic drug solubilizing agent, i.e., the propylene glycol ester as defined herein, should be substantially identical with that of the lipophilic drug. It is preferred that the octanol/saline partition coefficient of the lipid be similar, e.g., be within about 2 units (±2 units) relative to that of the active ingredient used in the present formulation.

When the propylene glycol ester containing at least about 60% by weight monoester based on the total weight of the propylene glycol ester is present in the amounts indicated hereinabove, the solubility of the lipophilic drug of the present formulation is enhanced. As a result, when the propylene glycol ester of $C_6$–$C_{18}$ fatty acids having at least about 60% by weight monoesters based on the total weight of the propylene glycol ester is present in effective amounts and is combined with an effective amount of the non-ionic surfactant and lipophilic drug, in accordance with the present invention, a preconcentrate, which is a self emulsifying drug delivery system (SEDDS), as defined herein, is formed. A microemulsion is formed when the preconcentrate comprising the propylene glycol esters used in the present invention, the water soluble non-ionic surfactant and the lipophilic drug are brought in contact with the aqueous medium or g.i. fluids of mammals. Surprisingly, the present inventor has found that the propylene glycol ester of $C_6$–$C_{18}$ fatty acids with at least about 60% by weight monoester, based on the total weight of the propylene glycol ester, provides drug solubility and co-surfactant properties essential to form the microemulsion when used in conjunction with the non-ionic water soluble surfactant and lipophilic drug and when the pharmaceutical composition of the present invention is brought in contact with aqueous medium, e.g., g.i. fluids. The inventor has additionally surprisingly found that propylene glycol diesters of the corresponding fatty acids do not aid in solubilizing the lipophilic drug. The present inventor has found that the presence of the specific lipophilic carrier used in the present invention not only provides the solubilization of the lipophilic drugs but also aids the SEDDS process.

The third essential component of the composition present is the water soluble non-ionic surfactant. It is preferred that the surfactant has a HLB (Hydrophilic Lipophilic Balance)

greater than 10 and more preferably greater than 12 and most preferably greater than 14. The surfactant of the present pharmaceutical composition is capable of forming a stable microemulsion when, in association with the propylene glycol ester and the drug, as described herein, it is brought into contact with aqueous fluid, such as in the G.I. tract. Examples of the preferred surfactant according to the present invention include polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives and the like, for example, NIKKOL HCO-50®, NIKKOL HCO-35®, NIKKOL HCO-40®, NIKKOL HCO-60® (from Nikko Chemicals Co. Ltd.); CREMOPHORE® (from BASF) such as CREMOPHORE RH40®, CREMOPHORE RH60®, CREMOPHORE EL®, TWEENS (from ICI Chemicals) e.g., TWEEN 20®, TWEEN 21®, TWEEN 40®, TWEEN 60®, TWEEN 80®, TWEEN 81®, CREMOPHORE RH 410®, CREMOPHORE RH 455® and the like.

The surfactant can include one or more surfactants having a HLB greater than 10. It can include any of the above-mentioned surfactants alone or in a combination with two or more surfactants selected from the above list. In the pharmaceutical composition of the present invention, it is preferred that the propylene glycol ester of $C_6$–$C_{18}$ fatty acid with at least about 60% by weight of mono-ester based on the total weight of the propylene glycol ester and surfactant be used in a weight ratio ranging from about 1:1 to about 1:500, respectively, and more preferably it the range of about 1:1 to about 1:20 and even more preferably from about 1:1 to about 1:4 and most preferably about 1:2 or 1:3.

It is also preferred that the ratio of drug to surfactant ranges from about 1:0.5 to about 1:500, more preferably from about 1:1 to about 1:500, more preferably from about 1:1 to about 1:20 and even more preferably from about 1:1 to about 1:4, and most preferably about 1:2.

In the composition of the present invention the three essential components are present preferably in the weight ratio of lipophilic drug:propylene glycol ester:surfactant ranging from about 1:0.5–500:0.5–500, respectively, and more preferably from about 1:1–20:1–20 and even more preferably from about 1:2–4:2–4.

In a preferred embodiment, the surfactant is present in equal to or greater amounts by weight than the propylene glycol ester.

Additives normally utilized in the pharmaceutical arts can also be added to the pharmaceutical composition and especially the carrier or carrier system. These include thickening, granulating, dispersing, flavoring, coloring, and stabilizing agents, other excipients, such as anti-oxidants (e.g., α-tocopherol, BHA, BHT, TBHQ and the like), preservatives (e.g., parabens), and the like.

The present pharmaceutical composition is prepared by uniformly and thoroughly mixing the "lipophilic drug, the solubilizing agent, and the surfactant together at room temperature or at slightly elevated temperature, such as temperatures up to about 60° C. until a clear solution is obtained, and then cooled to room temperature. The other additives indicated hereinabove are then thoroughly admixed therewith. In this preparation, the lipophilic drug remains in solution and does not crystallize or precipitate out.

An essential aspect of the pharmaceutical formulation of the present invention is that it forms a microemulsion when brought into contact with water or an aqueous medium. The microemulsion thus formed is thermodynamically stable when it comes into contact with the water or aqueous medium, as in the G.I. fluids of mammals. However, until the present formulation comes in contact with an aqueous medium, it is not a microemulsion; instead, when the various components are mixed, it forms what in the art is known as a preconcentrate of an emulsion (SEDDS), i.e., microemulsion pre-concentrate, i.e., a system capable of forming microemulsion respectively, on contact with water or aqueous system.

The microemulsion consists of substantially uniform and spherical droplets dispersed in a continuous medium. It is substantially non-opaque, i.e., is transparent or opalescent. The average particle size of the droplets in the present microemulsion are submicron. They are preferably less than about 200 nm, which explains the optical transparency. In a preferred embodiment, the average particle size is less than about 40 nm and more preferably less than about 20 nm. In an even more preferred embodiment, substantially all of the particles are less than about 40 nm and more preferably less than about 20 nm.

Thus, the preconcentrate (SEDDS) of the present invention when brought in contact with aqueous medium forms a microemulsion and is ideal for oral delivery systems for lipophilic drugs, since it is homogeneous, thermodynamically stable, has uniform droplet sizes and is optically clear. In a preferred embodiment the average particle size ranges from about 20 to about 40 nanometers.

By forming a microemulsion when in contact with aqueous medium, the present formulation minimizes and especially eliminates the risk that the lipophilic drug will precipitate or crystallize out of the aqueous dispersion, i.e., the microemulsion. In addition, it enhances the absorption of the lipophilic drug into the mammal.

Thus, the present formulation not only increases the solubility of the lipophilic drug in the pharmaceutical carrier, but also facilitates uniform absorption thereof in the treated mammal and enhances the bioavailability of the lipophilic drug.

Compositions of the present invention are preferably administered to mammals, such as dog, cat, horse, pig, mice, rat and especially humans. It is preferred that the pharmaceutical compositions of the present invention are administered orally in capsule, tablet, liquid-oral, powder, or the like or liquid for parental composition for intramuscular or intravenous administration. In a preferred embodiment, the invention provides a composition in a form appropriate or adapted for oral administration, in particular, in oral unit dosage form, e.g., in the form of tablets, capsules, drink solutions or dry powder for reconstitution; or a sohxlet form prepared by standard techniques known in the art, such as by spray coating on deposition. Especially suitable unit dosage forms for oral administration include encapsulated forms, e.g., soft or hard gelatin encapsulated forms, which is the preferred oral dosage forms or capsules made from non-gelatin materials.

Oral unit dosage forms in accordance with the present invention will preferably comprise from 1 μg to 600 mg and more preferably from 2 to 300 mg, e.g., 25, 50, 100, 125, 150, 200, 250 or 300 mg of lipophilic drug. The dosage of the drug and the number of times administered to the patient will vary depending on several factors, the age of the patient, the severity of the condition of the patient, past medical history, among other factors, and will be determined by the physician in his sound discretion without an undue amount of experimentation.

When the composition of the present invention is prepared in the form of a soft or hard capsule, the composition may be encapsulated in a gelatin shell which contains any conventional plasticizer. As the plasticizer which can be included in the gelatin capsule shell, one or more selected from the group consisting of glycerine, sorbitol, hexanetriol propylene carbonate, hexane glycol, sorbitans, tetrahydrofuryl alcohol ether, diethylene glycol monoethyl ether, 1,3-trimethyl-2-imidazolidone, dimethylisosorbide, etc. can be used without any limitation. However, it should be understood that the plasticizer which can be used in the present invention is not restricted to those mentioned above.

Capsule preparation according to the present invention can be prepared in a conventional machine by encapsulating the resulting preconcentrates of the emulsion of the present invention, e.g., the self-emulsifying pre-concentrate with or without the above-mentioned pharmaceutically acceptable additives.

Ethanol and other hydrophilic components are preferably substantially and even more preferably completely absent from the carrier system of the present invention. Since ethanol is preferably not present, especially in amounts sufficient to solubilize the lipophilic drug, there is less risk of precipitating or crystallizing the lipophilic drug in the pharmaceutical composition. If ethanol were present, and if it were present in the amounts usually found in pharmaceutical compositions containing cyclosporin or other lipophilic drug formulations described in the prior art, it would evaporate even when standing at room temperature, thereby causing possible crystallization and/or precipitation of the lipophilic drug. The absence of ethanol in these amounts in the present formulation prevents possible crystallization and precipitation of the lipophilic drug, thereby ensuring dosage uniformity, accurate blood levels of the lipophilic drug and consistent therapeutic performance.

The present pharmaceutical composition has several advantageous properties. It is non-volatile and non-hygroscopic and has a high boiling point. It has excellent compatibility with both soft and hard gelatin shell capsules, as well as with the other dosage forms, thereby providing excellent storage stability. Additionally, it provides greater solubility with higher drug loading, thereby providing smaller capsule size per unit dose of lipophilic drug and resulting in greater patient acceptance and compliance.

Moreover, if the oral dosage form is a capsule, there is an excellent compatibility of the carrier system of the present invention with hard or soft shell gelatin capsules, thereby preventing brittleness and leakage of the formulation during storage. Furthermore, the present pharmaceutical composition is a preconcentrate (SEDDS) which forms an emulsion and preferably fine emulsion and more preferably forms a microemulsion upon exposure to aqueous fluid (water, in e.g., the g.i. tract) which provides higher and uniform bioavailability. This characteristic further helps reduce the intra- and inter-subject variability associated with the absorption of the lipophilic active component, as well as minimize the effect of food on the absorption and bioavailability of the drug in mammals.

Moreover, there is no need for special precaution and procedure for the manufacturing, packaging and handling requirement during the preparation, storage and shipping of the product since ethanol is not present.

In addition, the compositions of the invention exhibit improved stability on storage as compared with compositions based on the use of ethanol or equivalent alkanols, such as those having 1–10 carbon atoms, and are, in particular, better adapted, e.g., for presentation in capsule, e.g. hard or soft gelatin capsule form. Preferred compositions in accordance with the present invention which are free or substantially free of ethanol or other hydrophilic components have the particular advantage of eliminating or substantially reducing packaging difficulties, e.g. in relation to the packaging of soft gelatin encapsulated forms.

The present pharmaceutical composition forms a more stable system and is capable of holding a larger amount of lipophilic drug than prior art formulations.

The present invention exhibits additional advantages over other carrier system which are comprised of glycerides including those having significant amounts of monoglycerides. The present inventor has found that there is greater compatibility between the carrier and drug when propylene glycol esters comprising at least 60% by weight monoester are utilized than when the carrier contains monoglyceride, even if the monoglyceride is present in larger amounts.

Moreover, the present inventor has found that the present carrier has advantages over those carrier systems comprising diesters. In the latter case, the diester does not exhibit the drug loading capabilities achieved by the present carrier, and thus, as a result, the size of the unit dosage form in the present invention is significantly smaller.

Moreover, unlike other systems which contain glycofural and other components which are non-GRAS, the present formulation contemplated by the present invention has GRAS status.

Furthermore, the present formulation can also be administered as a parenteral preparation for intra-muscular or even intravenous use with higher drug loading.

Moreover, in the formulations of the present invention in which a hydrophilic component is substantially absent, there is even better compatibility between the drug and the carrier, and in case of capsules as the oral dosage form, between the pharmaceutical composition as defined herein and the capsules, and particularly hard gelatin capsules. Moreover, in a preferred embodiment, it is preferred that fatty acid triglycerides are absent therefrom. The inventor has noted that the fatty acid triglycerides do not aid in solubilizing the drug; instead, their presence results in a larger oral dosage form, e.g., tablet or capsule. Consequently, it is preferred that they are substantially absent or even more preferably completely absent from the present pharmaceutical composition.

Thus the present pharmaceutical formulation has several advantages. It exhibits (I) an enhanced solubility of the drug thereby providing for higher drug loading and reducing the size of oral unit dosage of same (e.g., the size of the capsule will be reduced); (II) greater and uniform bioavailability; (III) better storage stability; (IV) greater compatibility with hard and soft gelatin capsules; (V) reduced inter and intra-subject variability, and (VI) minimal effect of food on the oral absorption of the drug. Furthermore, administration of the present formulation in the reduced size dosage forms, such as capsules, will facilitate greater patient acceptance and compliance. Moreover, unlike pharmaceutical compositions of the prior art containing alcohol of the present formulation, as defined herein does not require special handling during manufacturing or expensive specialized packaging.

The term "aqueous medium" as used herein, includes water, fluids containing water and in vivo media in mammals, such as the aqueous fluid present in the G.I. tract thereof.

As indicated to the contrary, the singular implies the plural and vice versa.

Moreover, it is to be understood, that in the preferred ratios given between the lipophilic drug and the propylene glycol esters, it is to be understood that the ester referred to hereinabove, unless indicated to the contrary, is the propylene glycol ester of $C_6$–$C_{18}$ fatty acid containing at least 60% monoester by weight based upon the total weight of propylene glycol ester. The ratio is not to be understood to be a ratio of the lipophilic drug to monoesters in the propylene glycol ester. The same is true with respect to the ratio of propylene glycol ester to surfactant and the ratio of drug:propylene glycol ester:surfactant.

Unless indicated to the contrary, all percentages and ratios are by weight.

The following examples further illustrate the present invention.

It is to be noted that the following examples utilize cyclosporin ibuprofen, paclitaxel and naproxen as the therapeutically active agent. However, these drugs are just exemplary, and the following examples should not be construed to limit the present invention. The present invention is applicable to lipophilic drugs, as defined herein, and is to be construed accordingly.

In Examples 1–7 and 9 & 10, the monoester of the propylene glycol ester is present in greater than 60% by weight and more preferably at 90% or greater by weight.

EXAMPLE 1

| INGREDIENT | MG/CAPSULES |
| --- | --- |
| Cyclosporin | 25 |
| Propyleneglycol Monoester of Caprylic Acid | 100 |
| Polyoxyethylene (20) sorbitan ester | 250 |
| TOTAL | 375 |

Procedure

Cyclosporin is dissolved in the propylene glycol monoester. The polyoxyethylene (20) sorbitan ester is added and the components are mixed until a clear solution is obtained.

EXAMPLE 2

| INGREDIENT | MG/CAPSULES |
| --- | --- |
| Cyclosporin | 100 |
| Propylene glycol monoester of Caprylic Acid | 175 |
| Polyoxyl 40 hydrogenated Castor oil | 525 |
| TOTAL | 800 |

Procedure

Cyclosporin is dissolved in the propylene glycol monoester of Caprylic Acid. Polyoxyl 40 hydrogenated Castor oil is added thereto. The components are mixed until a clear solution is obtained.

EXAMPLE 3

| INGREDIENT | MG/CAPSULES |
| --- | --- |
| Cyclosporin | 100 |
| Propylene glycol monocaprylate | 200 |
| Polyoxyl 35 Castor oil | 550 |
| TOTAL | 850 |

Procedure

Cyclosporin is dissolved in the propylene glycol monocaprylate. Polyoxyl 35 Castor oil is added thereto and the components are mixed until a clear solution is obtained.

EXAMPLE 4

| INGREDIENT | MG/CAPSULES |
| --- | --- |
| Cyclosporin | 100 |
| Propylene glycol monoester of Caprylic Acid | 250 |
| Polyoxyl 35 Castor oil | 510 |
| TOTAL | 860 |

Procedure

Cyclosporin is dissolved in the propylene glycol monoester. Polyoxyl 35 Castor oil is added thereto and the components are mixed until a clear solution is obtained.

EXAMPLE 5

| INGREDIENT | MG/CAPSULES |
| --- | --- |
| Cyclosporin | 25 |
| Propylene glycol monocaprylate | 75 |
| Polyoxyl 30 Castor oil | 130 |
| TOTAL | 230 |

Procedure

Cyclosporin id dissolved in the propylene glycol monocaprylate. Polyoxyl 30 Castor oil is added thereto, and the components are mixed until a clear solution was obtained.

EXAMPLE 6

| INGREDIENT | MG/CAPSULES |
| --- | --- |
| Cyclosporin | 25 |
| Propylene glycol monoester of Caprylic Acid | 100 |
| Polyoxyl 30 Castor oil | 130 |
| TOTAL | 255 |

Procedure

Cyclosporin id dissolved in the propylene glycol monoester of Caprylic Acid. Polyoxyl 30 Castor oil is added thereto and the components are mixed until a clear solution is obtained.

EXAMPLE 7

The following formation is prepared in accordance with the procedure described in Example 2.

| | |
|---|---|
| Ibuprofen | 200 mg |
| Propylene glycol monoester of Caprylic Acid | 250 mg |
| Polyoxyl 40 hydrogenated Castor oil | 350 mg |
| TOTAL | 800 mg |

EXAMPLE 8 and

Comparative Examples 1 and 2

The following formulations were prepared:

| EXAMPLE | FORMULATION | | INITIAL OBSERVATION | OBSERVATION AFTER 1 MONTH |
|---|---|---|---|---|
| Comparative Example 1 | Cyclosporin Propylene glycol Dicaprate-Caprylate, Diester > 90% Polyoxyl 35 Castor oil (CREMOPHORE EL 35 ®) | 100 mg 300 mg | Clear | Precipitation and Crystallization (after 1 week) |
| Comparative Example 2 | Cyclosporin Propylene glycol Laurate, Monoester, about 45 to 50% Polyoxyl 35 Castor oil (CREMOPHORE EL 35 ®) | 100 mg 200 mg 300 mg | Clear | Precipitation and crystal growth (after 2 weeks) |
| Example 8 | Cyclosporin Propylene glycol mono-Caprylate, monoester >90% Polyoxyl 35 Castor oil (CREMOPHORE EL 35 ®) | 100 mg 200 mg 300 mg | Clear | Clear solution after more than 3 months |

In each example, the cyclosporins were dissolved in the propylene glycol ester. The polyoxyl 35 castor oil was added thereto and the components were mixed until a clear solution was obtained.

The results are also tabulated in the above table.

When the pharmaceutical formulation contained the propylene glycol ester component as substantially the diester, as in Comparative Example 1, the cyclosporin precipitated and crystallized after 1 week of storage at 25° C. Thus, the presence of the diester did not aid in stabilizing the drug or solubilizing the drug in the carrier system. Moreover, the precipitated cyclosporin has poor and variable absorption in the g.i fluid, and as a result of the precipitation of the cyclosporin, the composition of the unit dosage form containing this formulation lacks uniformity. Therefore, the formulation in Comparative Example 1 is not suitable for any commercial use.

The above data also illustrate that there is criticality in the percentage of the monoester content present in the propylene glycol ester. The percentage of the monoester present plays, inter alia, a significant role in maintaining the solubility of Cyclosporins in the formulation. For example, as shown by the data in Comparative Example 2, when the pharmaceutical formulation contained a propylene glycol ester having a monoester content of 45 to 50% by weight, the cyclosporin crystallized out of the formulation within about 2 weeks of storage at 25° C., thereby making it unsuitable for practical commercial formulation.

However, the inventor has surprisingly found that when the propylene glycol ester having a monoester content of at least 60%, and preferably more than 90%, the formulation remained clear and there was no sign of precipitation or crystallization even after more than three months of storage at 25° C. This formulation therefore was deemed suitable for commercial use. Moreover, it was observed that the formulation of Example 8 further formed a self-emulsifying system, and more specifically, a microemulsion, when it was brought in contact with the aqueous medium as in the gastric fluid of the stomach.

The above results clearly indicate that the monoester content of Propylene glycol ester of $C_6$–$C_{18}$ fatty acids as described herein plays a significant role in the acceptable formulation of cyclosporins.

Thus, it is to be concluded from the experimental findings that the carrier provides maximum solubility or the highest drug loading capability for lipophilic drugs. Further, it did not show any precipitation and crystal growth on storage at 25° C., unlike the results found when the carrier system contained propylene glycol ester having mostly diester or 50% monoester by weight of the propylene glycol ester. Additionally, when combined with a surfactant having an HLB of at least 10, the present pharmaceutical formulation forms a self-emulsifying drug delivery system and preferably a microemulsion when brought in contact with the aqueous medium such as gastric fluids of stomach. This ability to form an emulsion is necessary for the uniform and maximum absorption of lipophilic drugs such as cyclosporin.

EXAMPLE 9

The procedure of Example 7 is followed except Naproxen was utilized in lieu of ibuprofen.

EXAMPLE 10

The procedure of Example 7 is followed except 50 mg of paclitaxel is utilized instead of ibuprofen and the total is 650 mg.

The above preferred embodiments and examples are given to illustrate the scope and spirit of the present invention. These embodiments and examples will make apparent to those skilled in the art other embodiments and examples. These other embodiments and examples are within the contemplation of the present invention.

Therefore, the present invention should be limited only by the appended claims.

What is claimed is:

1. A pharmaceutical composition comprising a pharmaceutically effective amount of a lipophilic drug in association with a pharmaceutical carrier, said carrier comprising (a) a lipophilic drug solubilizing effective amount of a propylene glycol ester of (a) $C_8$ fatty acid having at least about 90% by weight of monoester based on the total weight of the propylene glycol ester and (b) a non-ionic surfactant, said non-ionic surfactant being present in an amount sufficient to form a microemulsion with the propylene glycol ester and drug when brought in contact with an aqueous medium.

2. The pharmaceutical composition of claim 1 where the surfactant is polyoxyethylene sorbitan ester, the polyethoxylated product of hydrogenated vegetable oils, polyethoxylated castor oil or polyethoxylated hydrogenated castor oil.

3. The pharmaceutical composition according to claim 1 wherein the lipophilic drug and the propylene glycol ester of $C_8$ fatty acid with at least 90% by weight monoester, based on the total weight of propylene glycol ester, is present in a weight ratio ranging from about 1:0.5 to about 1:500, respectively.

4. The pharmaceutical composition according to claim 3 wherein the weight ratio ranges from about 1:1 to about 1:20.

5. The pharmaceutical composition according to claim 1 wherein the lipophilic drug and said surfactant are present in a weight ratio ranging from about 1:0.5 to about 1:500, respectively.

6. The pharmaceutical composition according to claim 5 wherein the weight ratio ranges from about 1:1 to about 1:20.

7. The pharmaceutical composition according to claim 6 wherein the weight ratio ranges from about 1:1 to about 1:4.

8. The pharmaceutical composition according to claim 1 wherein the weight ratio of said propylene glycol ester to said surfactant ranges from about 1:1 to about 1:500.

9. The pharmaceutical composition according to claim 8 wherein the weight ratio ranges from about 1:1 to about 1:4.

10. The pharmaceutical composition according to claim 1 wherein the propylene glycol ester of $C_8$ fatty acid contains at least about 95% monoester by weight based on the total weight of the propylene glycol ester.

11. The pharmaceutical composition according to claim 1 wherein said surfactant has an HLB value greater than 10.

12. A microemulsion of the pharmaceutical composition of claim 1.

13. The pharmaceutical composition according to claim 1 which is in oral dosage form.

14. The pharmaceutical composition according to claim 1 which is present in an injectable form or in a drink-solution.

15. The pharmaceutical composition according to claim 1 wherein the lipophilic drug, the propylene glycol ester of $C_8$ fatty acid having at least greater than about 90% by weight monoester based on the total weight of the propylene glycol ester and said surfactant are present in a weight ratio of 1:0.5–500:0.5–500, respectively, wherein the surfactant is present in equal to or greater amounts by weight than the propylene glycol ester.

16. The pharmaceutical composition according to claim 1 wherein the lipophilic drug is ibuprofen.

17. The pharmaceutical composition according to claim 1 wherein the lipophilic drug is paclitaxel.

18. A method of forming a microemulsion comprising (a) thoroughly mixing a pharmaceutically effective amount of lipophilic drug with (i) a drug solubilizing effective amount of propylene glycol ester of $C_8$ fatty acid with at least about 90% by weight of monoester based on the total weight of the propylene glycol ester; and (ii) a non-ionic surfactant having a HLB value greater than 10, said surfactant being present in sufficient amount to form a microemulsion with the lipophilic drug and said propylene glycol ester when brought in contact with an aqueous medium and (b) contacting said product of (a) with aqueous medium.

19. A method of increasing the drug loading ability of a lipophilic drug in a pharmaceutical composition, said method comprising thoroughly mixing said lipophilic drug with (a) a drug solubilizing effective amount of a propylene glycol ester of $C_8$ fatty acid with at least about 90% by weight monoester based on the total weight of the propylene glycol ester and (b) a non-ionic surfactant having a HLB value greater than 10, said surfactant being present in amounts sufficient to form a microemulsion with said lipophilic drug and said propylene glycol ester when brought in contact with an aqueous medium.

20. A method of enhancing the bioavailability of a lipophilic drug in a patient during therapy comprising orally administering to said patient undergoing drug therapy the pharmaceutical composition according to claim 1.

21. A method of orally administering a pharmaceutical composition containing a lipophilic drug to a patient in need thereof comprising administering to said patient a pharmaceutical composition comprising a pharmaceutically effective amount of a lipophilic drug, a drug solubilizing effective amounts of a propylene glycol ester of $C_8$ fatty acid with at least 90% by weight monoester based on the total weight of the propylene glycol ester and a sufficient amount of a non-ionic surfactant having a HLB greater than 10, said surfactant being present in sufficient amounts to form a microemulsion with said lipophilic drug and said propylene glycol ester when brought into contact with water.

22. The method according to claim 21, wherein the lipophilic drug is ibuprofen.

23. The method according to claim 21 wherein the lipophilic drug is naproxen.

24. The method according to claim 21 wherein the lipophilic drug is paclitaxel.

25. A method of enhancing the bioavailability of a lipophilic drug in a patient during drug therapy comprising orally administering to said patient the pharmaceutical composition according to claim 1.

26. A pharmaceutical carrier for association with a lipophilic drug, said carrier comprising (a) a lipophilic drug solubilizing effective amount of a propylene glycol ester of $C_8$ fatty acid having at least about 90% by weight of monoester based on the total weight of the propylene glycol ester and (b) a non-ionic surfactant, said non-ionic surfactant being present in an amount sufficient to form a microemulsion with the propylene glycol ester and drug when brought into contact with an aqueous medium.

* * * * *